United States Patent [19]
Skladnev et al.

[11] Patent Number: 5,941,822
[45] Date of Patent: Aug. 24, 1999

[54] APPARATUS FOR TISSUE TYPE RECOGNITION WITHIN A BODY CANAL

[75] Inventors: Victor N. Skladnev, Vaucluse; Richard L. Thompson, Killarney Heights, both of Australia; Irwin Wunderman, Mtn View, Calif.; David J. Bull, Epping, Australia

[73] Assignee: Polartechnics Limited, Sydney, Australia

[21] Appl. No.: 08/818,930

[22] Filed: Mar. 17, 1997

[51] Int. Cl.$^6$ ........................................................ A61B 5/00
[52] U.S. Cl. ............................ 600/407; 600/475; 600/477
[58] Field of Search ..................................... 128/664, 665, 128/633, 634; 600/473, 476, 310, 342, 372, 373, 178, 407, 475, 477

[56] References Cited

U.S. PATENT DOCUMENTS

| | | | |
|---|---|---|---|
| 3,647,299 | 3/1972 | Lavallee | 356/41 |
| 3,910,701 | 10/1975 | Henderson et al. | 356/39 |
| 3,994,590 | 11/1976 | Di Martini et al. | 356/178 |
| 4,587,421 | 5/1986 | Robertson | 250/239 |
| 4,856,527 | 8/1989 | Karcher et al. | 128/634 |
| 4,942,877 | 7/1990 | Sakai et al. | 128/633 |
| 5,036,853 | 8/1991 | Jeffcoat et al. | 128/634 |
| 5,275,160 | 1/1994 | Lilge et al. | 128/634 |
| 5,411,024 | 5/1995 | Thomas et al. | 128/634 |
| 5,413,099 | 5/1995 | Schmidt et al. | 128/633 |
| 5,417,207 | 5/1995 | Young et al. | 128/634 |
| 5,427,093 | 6/1995 | Ogawa et al. | 128/633 |
| 5,520,177 | 5/1996 | Ogawa et al. . | |

OTHER PUBLICATIONS

Mendelson, Ph.D. et al., Design and Evaluation of a New Reflectance Pulse Oximeter Sensor, Medical Instrument, vol. 11, No. 4, pp. 187–173, 1988.

Neuman, M.R., In Medical Instrumentation: Application and Design, pp. 265–266, Webster, J.G. (ed) 2nd Ed. Boston: Houghton Miffliin, 1992.

*Primary Examiner*—Marvin M. Lateef
*Assistant Examiner*—Shawna J. Shaw
*Attorney, Agent, or Firm*—Gottlieb, Rackman & Reisman, P.C.

[57] ABSTRACT

A method and apparatus for tissue type recognition for use within the narrow confines of body canals and which can quickly produce an objective identification of the tissue types including the presence of pre-cancerous and cancerous activity. Possible configurations for the probe include endocervical probe configurations which make measurements in directions orthogonal to the long axis of the probe and configurations where multiple probe "tips" are arranged in a "wood drill" configuration. The apparatus has a measurement section that has at least one source of electromagnetic radiation such as a light emitting diode, a barrier which acts to confine the direction that the radiation can take and a detector such as a photodiode beyond the barrier, which is able to detect the radiation after it has been backscattered from tissue in close proximity to the surface of the cylinder. In the vicinity of these components one or more electrodes may also be positioned on the surface of the cylinder such that they are able to contact the tissue under examination thereby enabling simultaneous electrical property measurements to be made. The radiation source and the electrodes receive electrical signals produced by a programmed controller. The radiation detector and the electrode signals are processed by the controller. Comparator means in the controller are used to compare the signals with known values to thereby identify the tissue type.

7 Claims, 3 Drawing Sheets

APPARATUS FOR TISSUE TYPE RECOGNITION WITHIN A BODY CANAL

FIELD OF THE INVENTION

The present invention relates to a method and apparatus for identifying different tissue types within body canals such as the endocervical canal including those displaying modifications involving pre-cancerous or cancerous stages, diseased tissue, and those that are in a transitional stage. The identification of different tissue types is provided via a set of measurements of the tissue's physical properties and in particular the optical and electrical properties of the tissues.

BACKGROUND

The medical profession often needs to have an objective assessment of the health of the tissue of a patient. The patient may have suffered tissue damage as a result of accidental or deliberate trauma as for example during a surgical operation. The patient may also be suffering some other more persistent irritation as a result, for example, of being confined to bed which can lead to bed sores. It is valuable for a medical practitioner to be able to tell in advance the type of treatment that would benefit the patient.

It is well known, for example, that early detection of tissues displaying pre-cancer or cancer modifications is important for successful medical treatment. We have already disclosed an apparatus and method for carrying out this detection. The invention described in this application represents a significant improvement on the apparatus disclosed in patent application Ser. No. 08/332,830, assigned to the same assignee as the current invention.

Previous probes have had optical components distributed along the length of the probe, for example optical sensors extending via fiber optics to components capable of converting the optical signals into electrical impulses.

Cancerous activity in the human body frequently arises in canals such as the endocervical canal. Visual observation of the health of tissue within these canals is not feasible. For example, in some cases cervical cancer commences in the endocervical canal so it is important that this region be checked for the state of health of the tissue. Because of the narrowness of the canal particularly in younger women, any device which is required to enter must necessarily be of small diameter. A typical maximum permissible diameter is of the order of 3 mm.

It has been established that tissue typing can be determined by making optical and electrical measurements on the tissue. In the narrow confines of the endocervical canal, making optical backscattering measurements on the tissue presents significant difficulties. These measurements need to be confined to small areas in order to maintain the sensitivity of the device to the tissue type. Measurements made over larger areas will necessarily average the properties over that area and will not disclose small regions of abnormality.

To perform optical property measurements over a small area the technology available up to the present has relied on the use of optical fibers to guide the light to and from the area to be examined. This is feasible where the area is relatively accessible. In the case of canals, however, access is limited by the requirement that the device may have to be only of the order of 3 mm diameter, has to look outward at the canal surface and may need to make measurements at several wavelengths.

SUMMARY OF THE INVENTION

The present invention overcomes these difficulties and limitations in a novel manner. The device also provides for electrical measurements to be made at the same time on essentially the same area of tissue to aid the diagnosis.

The present invention concerns a hybrid probe for both electrical and optical measurements in which the optical pathway and the optical sensors comprise elements located within a hybrid chip structure that is compact. The present invention greatly expands the possible configurations for the probe, including endocervical probe configurations, which make measurements in directions orthogonal to the long axis of the probe and configurations where multiple probe "tips" are arranged in a "wood drill" configuration that allows simultaneous investigation of multiple points on the cervix.

It is an object of the present invention to provide a method and apparatus for tissue type recognition which permits use within the narrow confines of body canals and which can quickly produce an objective identification of the tissue types including the presence of pre-cancerous and cancerous activity.

The apparatus comprises a measurement section in the form of a cylinder of circular, elliptical or similar cross-section in which is located at least one source of electromagnetic radiation such as a light emitting diode, a barrier which acts to confine the direction that the radiation can take and a detector such as a photodiode beyond the barrier, which is able to detect the radiation after it has been backscattered from tissue in close proximity to the surface of the cylinder. In the vicinity of these components one or more electrodes are also positioned on the surface of the cylinder such that they are able to contact the tissue under examination thereby enabling nearly simultaneous electrical property measurements to be made. The location of these electrodes should be such as to ensure that the electrical measurements are made of essentially the same area of tissue as those that are measured optically.

It is important to isolate light emitting and light receiving elements of the probe from one another. The hybrid probe is designed to examine areas of tissue having a diameter of the order of 2 mm, which requires that photodiode detectors be placed in close juxtaposition with light emitters yet optically isolated so that light signals do not pass directly from an emitter to a detector without intervention (i.e. backscattering) by the tissue under examination. This is accomplished in the present invention by the use of metal barriers. The metal barriers also shield the detector circuitry from electrical interference carried by current pulses that must be applied to the LEDs to induce them to emit light. The metal barrier may be left floating or grounded, but can also serve an additional role as an electrode for making electrical measurements to replace or supplement the two or three noble metal electrodes adjacent to the hybrid circuit normally used for the electrical measurements to be made on the tissue.

In addition the hybrid structure provides a preamplifier in close proximity to the photodiodes to amplify the small current from the photodiode detectors and feed it to the electronics in the handle of the probe and from there to the analysis circuitry.

An additional advantage of the hybrid structure of the present invention is that it eliminates the inefficiency of the coupling of light emitters to optical fibers that carry the emitted light in prior systems, and also eliminates uncertainties associated with the bending or heating of the optical fibers. It is also significantly less expensive to manufacture the hybrid than the prior extended circuit.

The radiation source and the electrodes receive electrical signals produced by a controller programmed according to a predetermined sequence. The radiation detector and the electrode signals are processed by the controller. Comparator means in the controller are used to compare the signals with known values to thereby identify the tissue type.

The method of identification of the tissue suspected of being physiologically changed as a result of pre-cancerous or cancerous activity comprises the steps of, irradiating the tissue with electromagnetic radiation receiving the radiation backscattered by the tissue generating mathematical transforms of the detected signals and comparing these with a catalogue of key features of normal and abnormal tissue types.

The quality of the diagnosis is enhanced by supplying electrical signals to electrodes in touch with the tissue, measuring the resulting electrical response of the tissue, transforming these electrical signals and comparing them with a catalogue of features of normal and abnormal tissue types.

DETAILED DESCRIPTION OF A PREFERRED EMBODIMENT

Figure 1:
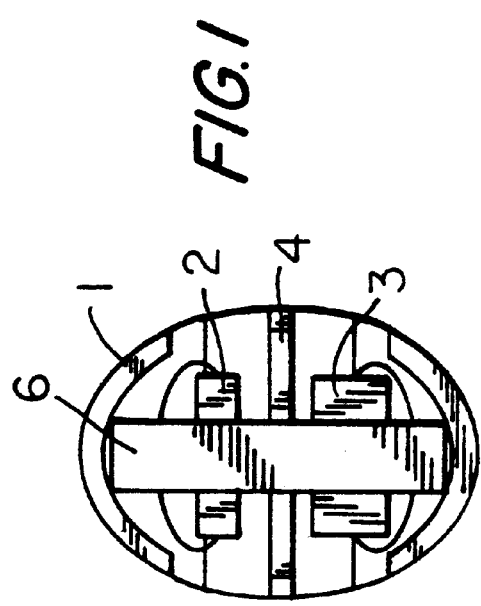
FIG. 1 is a cross section of the probe tip in the vicinity of the opto-electronics.

The use of both optical and electrical measurements to detect pre-cancerous and cancerous states of tissue has been described in copending patent application Ser. No. 08/332, 830, assigned to the same assignee, the text of which is incorporated herein by reference. The device described in that application, by virtue of its configuration, had application only to tissue which is accessible by a relatively large device. The confines of body canals precluded its use in such situations. The probe of the present invention is useful to detect the onset of precancer or cancer within the endocervical canal or os in addition to making measurements on the outer parts of the cervix.

The present invention uses semiconductor dice packed into a small volume to keep the size of the assembly small enough to enter the canal to make optical measurements within these confines. The electrical measurements do not present the same problems arising from the small size of the probe since small electrodes can readily be fabricated. The placement of the electrodes is, however, a critical issue.

In the endocervical probe, there are two complete optical and electrode systems on opposite faces of the cylinder, in order to obviate the need to manipulate the probe through more than a half revolution during examination by the doctor. This device overcomes the inability to make optical measurements of this type using fibers, because of the infeasibility of bending optical fibers through a right angle to make measurements accurately in a radial direction out of the probe.

In some applications the probe will typically be held in one hand while the other is used to hold a speculum. This means that the probe cannot be passed from hand to hand during the probing operation. As a consequence rotation of the probe during the examination through more than 180 degrees is difficult. Since a full circle of examination is necessary during probing, it has been arranged for the probe to scan in two opposing directions at once. This enables a full scan of the bore of the canal to be performed with only a 180 degree rotation of the probe. Additional sensing systems could in theory be mounted around the barrel of the probe and thereby reduce the amount of rotation needed but in practice this may not be realistic.

In addition to the need to prevent radiation from the emitter from reaching the detector directly, it is important that the angle of illumination by the emitter and the angle of acceptance by the detector be controlled. To this end in the present invention shields have been installed around the opto-electronics section to confine the angles. The area of tissue that affects the amount of backscattered radiation is thus limited, leading to a more accurate diagnosis of the tissue type.

Another important feature of the present invention is the inclusion of electrostatic shielding around the opto-electronics. The probe will be employed on patients who will not necessarily be grounded electrically. Their bodies may therefore have fluctuating potentials of the order of volts that could arise from electromagnetic coupling with the mains wiring of the building or other electrical devices in the vicinity. These signals could be coupled to the circuitry in the probe and interfere with the detection of the backscattered light signals. Provision of a shield around this part of the probe will prevent this coupling.

Figure 2:
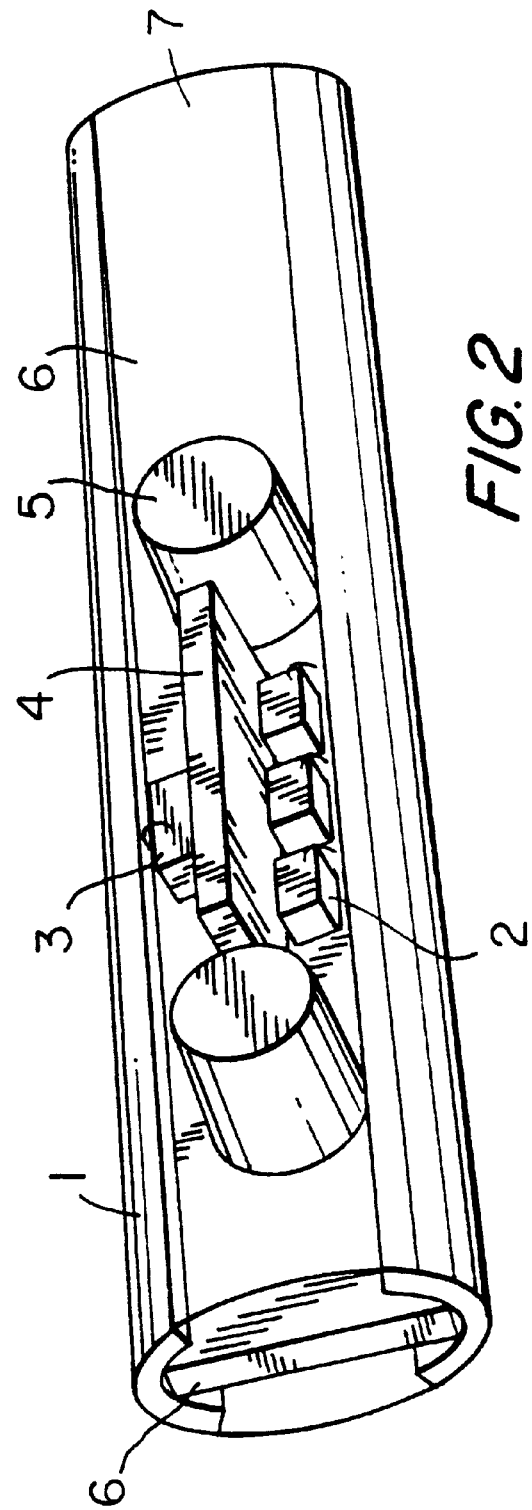
FIG. 2 is a side view of the probe tip in the same region.
Figure 3:
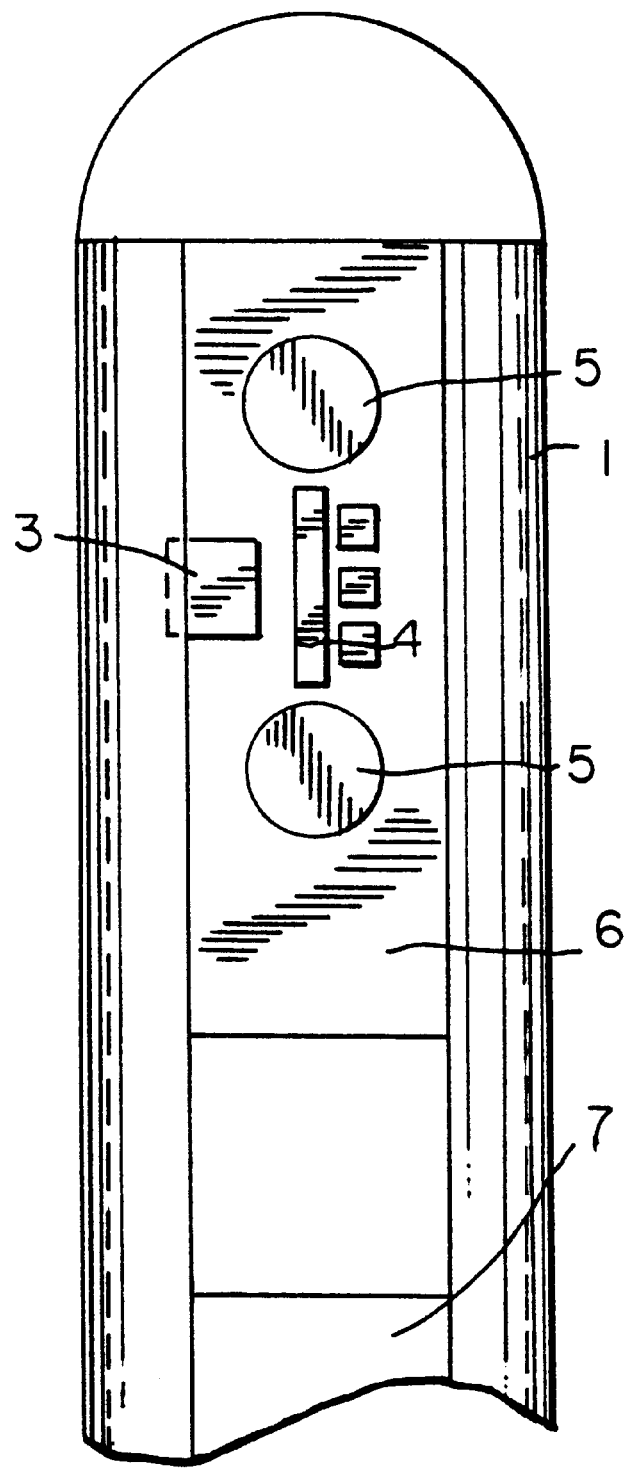
FIG. 3 is a side view showing the rounded end of the probe tip.

FIG. 1 shows a cross section of a probe comprising emitters and detectors that is fitted with electrodes in the vicinity of the opto-electronics section. FIG. 2 is a perspective view of the same part of the probe. The body of the probe is fitted with optically opaque shields 1 that confine the emitted and detected radiation to the areas that are to be examined. Radiation leaving the emitters at other angles is blocked. The area scanned by the probe is at least partially defined by the shields 1. If the shields 1 are made larger, the area being scanned will be further confined, thereby improving resolution, but there are limits to this set by the need to allow an adequate amount of radiation to reach the tissue and to be backscattered to the detector. If this area is too small, the signal will be swamped by optical and electrical noise. An appropriate compromise has therefore to be reached on these dimensions. We have found that the size of this area is contingent on the efficiency of the light emitting diodes (LEDs) 2 employed as the radiation sources. There is a trend towards increasing efficiency as the technology improves so it is difficult to put a firm figure on the dimensions that should be employed. From a physiological point of view there is probably little point in reducing the width of the window above the opto-electronics to less than 1.5 mm. Areas of abnormal tissue smaller than this are unlikely to be a danger to the health of the patient since they will most likely spontaneously clear in a relatively short time.

Mounted on the supporting circuit board 6 are LED dice 2. In this embodiment three are employed but the number can vary from one upwards according to the requirements of the probe and the space available to fit them. Also mounted on the board are detector dice 3, typically silicon photodiodes, which are shielded from the LEDs by the barriers 4. These barriers act both as optical and electrostatic shields. The current through the LEDs is many orders of magnitude greater than the detector signal so shielding is important. The barriers are typically electrically conductive and may be grounded but not necessarily so. To stabilize the components they may be embedded in a transparent epoxy filler which allows the electrodes to extend beyond its surface.

In this embodiment two electrodes 5 are shown mounted at each end of the opto-electronic assemblies. Their positions and number can differ from these but the arrangement shown is typical. The positioning of the electrodes needs to ensure that the electrical properties are measured on the same area of tissue as that measured for its optical properties. By placing the electrodes as shown in FIG. 2 this is largely achieved. The barrier 4 described above can also be used as an electrode which is even closer to the tissue being observed optically.

The space in the barrel of the probe can be filled with transparent resin to fix the components in place. Small amounts of opaque resin can also be added between the ends of the barrier 4 and the electrodes 5 to prevent light from leaking around the ends of the barrier.

The LEDs 2 in the assembly can be driven by the controller's electrical signals passing down the shaft 7 from the upper part of the probe to the tip section described above. Similarly the signals from the detectors can be fed to amplifiers situated a short distance up the shaft 7 of the probe. The distance should be kept as short as possible since the signals from the detectors are of very low magnitude so are sensitive to electrical interference derived either from external sources or from the drive signals on their way to the LEDs.

A critical feature of this arrangement arises from the need to take special care with the shielding of the wiring from the detectors 3 to their amplifiers. The currents flowing in this wire may be of the order of nanoamperes. The drive current to the nearby LEDs may be as high as 100 milliamperes. The ratio of these currents is huge so shielding is vital. In addition, the patient's body may have substantial voltage signals present because of adjacent wiring or other electrical equipment being operated nearby. The detector circuit must therefore be shielded from this source of interference as well. This is achieved by the use for example of multilayer circuit boards 6 to convey the signals. The disposition of the signals flowing in the tracks on these boards must be chosen carefully to avoid unwanted capacitive or electromagnetic coupling.

The cross-sectional shape of the probe illustrated in FIG. 1 is shown as elliptical. It can also be circular or can be flattened at the optical faces. The elliptical shape has the advantage of reducing the distance between the LEDs and the tissue surface and thereby improving the efficiency of the optical system in terms of the detected signals.

The optical layout needs to be carefully planned because of the conflicting demands made on it. The radiation signal reaching the tissue needs to reach a level sufficient to compete with the ambient light level being employed for the operator's visual needs. LEDs have limited light output so there are advantages in having as much as possible of this radiation reach the tissue. To achieve this the LEDs 2 should be placed as close as possible to the tissue. It is a fact that the efficiency of LEDs continues to improve so the above considerations may become less important in the future. There are two limits on how small the distance from the top of the LEDs to the tissue can be made. The first of these is the need to accommodate the bond wires from the top of the LEDs which tends to loop upward from the surface of the die. The second arises from optical considerations. It is important to control the direction and angle of the illumination of the tissue surface so that probes behave consistently. If the distance between the opto-electronics and the tissue varies, the sensitivity of the device will vary. Tissue recognition will thereby be impaired. The distance from the LEDs 2 to the tissue surface should therefore be kept large enough that assembly tolerances do not lead to uncontrolled variability between probes. Since the position and size of the LED top surface can typically be controlled to within plus or minus 25 micrometers, this uncertainty should not be more than, say, 5% of the LED to surface distance. That distance should therefore be not less than 0.5 millimeter. The same considerations apply to the detectors 3.

The lateral placement of the dice is similarly controllable to only 25 micrometers so this needs to be factored in to the geometric considerations. More deeply placed dice will be less sensitive to errors in placement.

The lateral placement also affects the diagnostic ability of the device by modifying the depth of penetration of the radiation prior to its return to the detector. It is important therefore that the placement be chosen to achieve the desired depth of penetration bearing in mind the tolerances on the accuracy that can be maintained. In general the closer the opto-electronics components 2 and 3 are to the barrier 4 the smaller the depth of penetration.

The use of an elliptical shape for the probe has the additional advantage that physical penetration of canals can be eased because the circumference of such a probe is lower than that of a circular one.

The controller, which is not illustrated, drives the radiation sources and measures the signals from the detector and from the electrodes when they are included. It also applies a small current to the LEDs 2 and measures the voltage drop to determine the temperature of the LEDs. It then calculates a correction for the radiation output from the LEDs and adjusts the measured values of the detector signal accordingly.

The controller performs manipulations on the corrected signals from the probe and arrives at a decision as to the tissue type by comparing the data with a catalogue of data of known tissue types. The decision is then communicated to the operator via one of several means such as by means of colored lights on the probe, by an audible tone, or by a display on the controller.

Figure 4:
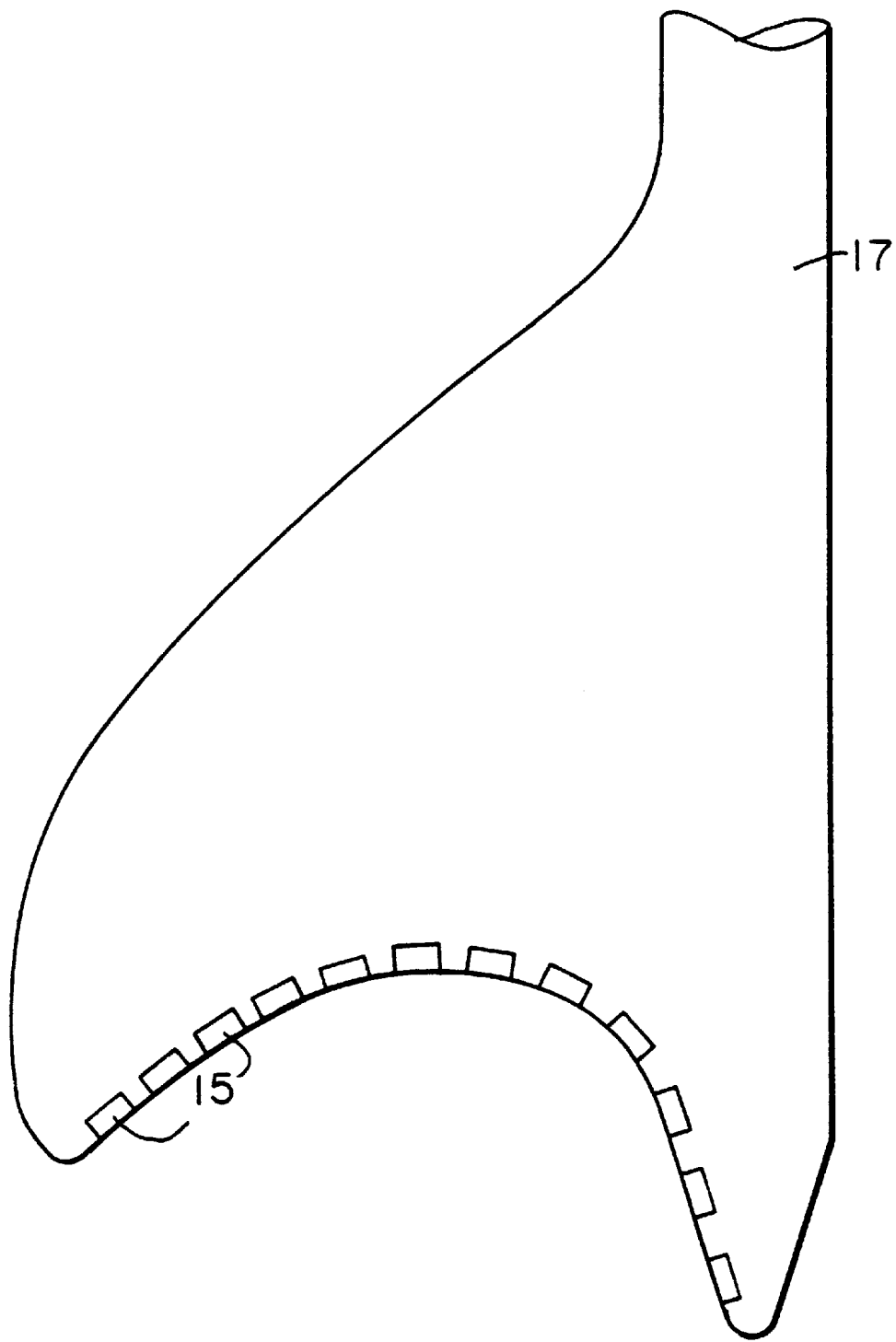
FIG. 4 depicts an endocervical probe having a "wood drill" configuration incorporating a plurality of hybrid probe "tips".

FIG. 4 depicts the "wood drill" configuration where the individual probe tips 15 are arranged in a pattern with respect to the probe shaft 17, enabling the doctor to scan a large number of points on the cervix in one operation. It enables coverage of the ecto- and endo-cervical regions in one operation.

Although the invention has been described in detail in terms of its presently preferred embodiments, it should be understood that the invention is capable of being practiced in other manners and accordingly is defined by the proper legal scope of the following claims.

What is claimed is:

1. Apparatus for identifying tissue within a body canal which is suspected of being physiologically changed as a result of pre-cancerous or cancerous activity, said apparatus comprising a plurality of optical and electrode systems, each such system comprising
a light emitting die emitting light in response to a drive signal and configured to irradiate said tissue;
a detector die configured to receive that radiation after it has been backscattered by said tissue and to provide a responding signal;
a barrier sited between the two dice to provide optical and electrical isolation between the two;
an electrode configured to supply electrical signals to said tissue and to measure the response of the tissue;

the components above being configured in a probe of circular or similar cross section small enough to enter the said canal;

a controller coupled to the emitters, the detectors and the electrodes that supplies the necessary drive signals and receives the responses, said controller comprising a processor to categorize said tissue, and a comparator for comparing the categorization of said tissue with expected tissue types from a catalogue so as to identify said tissue, and an indicator arrangement for indicating to a user the tissue type identified.

2. Apparatus as claimed in claim 1 wherein said configurations of opto-electronics and electrodes are situated on more than one face of the probe.

3. Apparatus as claimed in claim 1 wherein said configurations of opto-electronics and electrodes are situated on a cone-shaped probe.

4. Apparatus as claimed in claim 1 in which the wiring from the detectors is shielded electrically by mounting conductive metal surfaces in close proximity to the said wiring to reduce the capacitive coupling of that wiring to the circuit that feeds current to the light emitters in the probe tip and to reduce the capacitive coupling to the patient who is being examined, thereby reducing the amount of cross coupling and electrical interference added to the detector signal.

5. An apparatus as claimed in claim 1 in which a current is applied to LEDs and the voltage drop is measured to determine the temperature of the LEDs to enable calculation of a correction for the radiation output from the LEDs in order to apply an adjustment to the measured values of the detector signal.

6. Apparatus as claimed in claim 2 in which the wiring from the detectors is shielded electrically by mounting conductive metal surfaces in close proximity to the said wiring to reduce the capacitive coupling of that wiring to the circuit that feeds current to the light emitters in the probe tip and to reduce the capacitive coupling to the patient who is being examined, thereby reducing the amount of cross coupling and electrical interference added to the detector signal.

7. Apparatus as claimed in claim 3 in which the wiring from the detectors is shielded electrically by mounting conductive metal surfaces in close proximity to the said wiring to reduce the capacitive coupling of that wiring to the circuit that feeds current to the light emitters in the probe tip and to reduce the capacitive coupling to the patient who is being examined, thereby reducing the amount of cross coupling and electrical interference added to the detector signal.

* * * * *